(12) United States Patent
Baba

(10) Patent No.: US 9,855,159 B2
(45) Date of Patent: Jan. 2, 2018

(54) STENT AND STENT DELIVERY SYSTEM

(71) Applicant: TERUMO KABUSHIKI KAISHA, Tokyo (JP)

(72) Inventor: Takeshi Baba, Fujinomiya (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 27 days.

(21) Appl. No.: 14/035,136

(22) Filed: Sep. 24, 2013

(65) Prior Publication Data

US 2014/0025153 A1    Jan. 23, 2014

Related U.S. Application Data

(63) Continuation of application No. PCT/JP2012/055774, filed on Mar. 7, 2012.

(30) Foreign Application Priority Data

Mar. 29, 2011 (JP) .................................. 2011-072476

(51) Int. Cl.
*A61F 2/958* (2013.01)
*A61F 2/915* (2013.01)

(52) U.S. Cl.
CPC ............. *A61F 2/958* (2013.01); *A61F 2/915* (2013.01); *A61F 2002/91558* (2013.01);
(Continued)

(58) Field of Classification Search
CPC .................. A61F 2/82; A61F 2002/821; A61F 2002/823; A61F 2002/825;
(Continued)

(56) References Cited

U.S. PATENT DOCUMENTS 5,922,020 A    7/1999    Klein et al.

6,416,543 B1 *  7/2002   Hilaire .................... A61F 2/91
623/1.15
(Continued)

FOREIGN PATENT DOCUMENTS

EP         0887051 A1     6/1998
JP     2000-084090 A      3/2000
(Continued)

OTHER PUBLICATIONS

Extended Eurpoean Search Report dated Sep. 16, 2014, issued by the European Patent Office in corresponding European Patent Application No. 12762801.4 (5 pgs).
Office Action (Notification of First Office Action) dated Feb. 6, 2015, by the State Intellectual Property Office of People's of Republic of China in corresponding Chinese Patent Application No. 201280003902.X, and an English Translation of the Office Action. (13 pages).
(Continued)

*Primary Examiner* — Christopher L Templeton
*Assistant Examiner* — George J Ulsh
(74) *Attorney, Agent, or Firm* — Buchanan Ingersoll & Rooney PC

(57) ABSTRACT

A stent includes a wavy-shaped member extending circumferentially, and expandable and contractable in the radial direction of the stent. The wavy-shaped member includes a pair of straight parts, an apex part and an opening. The ends of the apex part are connected to the straight parts. The opening is positioned at least in the apex part. The apex part has a link part at the outer circumference side of the opening, and a base part at the inner circumference side of the opening. The base part has a curved inner circumference and the link part lies across a vertex of the base part. The width of the link part in relation to the circumferential direction of the stent is smaller than the width of the base part in relation to the circumferential direction of the stent, at the vertex of the base part.

14 Claims, 8 Drawing Sheets

(52) U.S. Cl.
CPC ............... *A61F 2230/0013* (2013.01); *A61F 2230/0054* (2013.01); *F04C 2270/0421* (2013.01)

(58) Field of Classification Search
CPC .......... A61F 2002/826; A61F 2002/828; A61F 2/86; A61F 2/89; A61F 2/90; A61F 2/91; A61F 2/915; A61F 2002/9155; A61F 2002/91558; A61F 2002/91583
USPC ............................................... 623/1.11–1.15
See application file for complete search history.

(56) References Cited

U.S. PATENT DOCUMENTS

| | | | |
|---|---|---|---|
| 2001/0016770 A1* | 8/2001 | Allen et al. ................ | 623/1.15 |
| 2001/0032011 A1 | 10/2001 | Stanford | |
| 2004/0243217 A1 | 12/2004 | Andersen et al. | |
| 2005/0283228 A1 | 12/2005 | Stanford | |
| 2009/0204202 A1 | 8/2009 | Dierking et al. | |

FOREIGN PATENT DOCUMENTS

| | | |
|---|---|---|
| JP | 2000-516486 A | 12/2000 |
| JP | 2004-329790 A | 11/2004 |
| JP | 2005-511139 A | 4/2005 |
| JP | 2009-240613 A | 10/2009 |
| JP | 2009-240796 A | 10/2009 |
| WO | WO 98/05270 A1 | 2/1998 |
| WO | 03022178 A1 | 3/2003 |
| WO | 03/047463 A1 | 6/2003 |
| WO | 2007005800 A1 | 1/2007 |

OTHER PUBLICATIONS

International Search Report (PCT/ISA/210) dated May 29, 2012, by the Japanese Patent Office as the International Searching Authority for International Application No. PCT/JP2012/055774.

Office Action (Notification of Second Office Action) dated Sep. 17, 2015, by the State Intellectual Property Office of People's of Republic of China in corresponding Chinese Patent Application No. 201280003902.X, and an English Translation of the Office Action. (10 pages).

Japanese Office Action ("Notice of Reasons for Rejection") dated Apr. 19, 2016 in counterpart Japanese Application No. 2013-507322 (9 pages, with English translation).

Office Action (Notification of the Third Office Action) dated Mar. 7, 2016, by the Chinese Patent Office in corresponding Chinese Patent Application No. 201280003902.X, and an English Translation of the Office Action. (9 pages).

Office Action (Notification of Fourth Office Action) dated Sep. 14, 2016 by the State Intellectual Property Office of People's of Republic of China in corresponding Chinese Patent Application No. 201280003902.X, and an English Translation of the Office Action. (11 pages).

English Translation of the Office Action ("Decision of Rejection") dated May 11, 2017 by the State Intellectual Property Office (SIPO) of the People's of Republic of China in corresponding Chinese Patent Application No. 201280003902.X. (10 pages).

Office Action (Notice of Reasons for Rejection) dated Dec. 8, 2015, by the Japanese Patent Office in corresponding Japanese Patent Application No. 2013-507322, and an English Translation of the Office Action. (7 pages).

\* cited by examiner

EXPANDED STATE

STENT AND STENT DELIVERY SYSTEM

CROSS REFERENCES TO RELATED APPLICATIONS

This application is a continuation of International Application No. PCT/JP2012/055774 filed on Mar. 7, 2012, and claims priority to Japanese Application No. 2011-072476 filed on Mar. 29, 2011, the entire content of both of which is incorporated herein by reference.

TECHNICAL FIELD

The present invention generally relates to a stent and a stent delivery system.

BACKGROUND ART

A stent delivery system is a medical device used for improving a stenosis or occluded part in a lumen in a living body. The stent delivery system is provided with an inflatable balloon which is disposed on the outer circumference of a distal end portion of a hollow shaft section, and a stent which is composed of wavy linear members, is disposed on the outer circumference of the balloon and is expanded by inflation of the balloon.

The stent is caulked (mounted) onto the balloon while the balloon is in a radially contracted state. After arrival in a target part (stenosis or occluded part), the balloon is inflated to bring the stent into plastic deformation, whereby the stent is put indwelling (indwelled) in secure contact with the inner surface of the target part. In this instance, depending on the state of the target part or the way in which the balloon is inflated, the stent may fail to spread uniformly in the circumferential direction, so that the stent may be unable to display its intended performance.

In consideration of the above-mentioned problem, for example, there is a stent wherein apex parts (opposed stop surfaces) of linear members (struts) are engaged with each other so that hinge regions of the linear members will not be opened in excess of a predetermined angle, whereby non-uniform expansion of the stent in the circumferential direction is prevented. An example of this stent is disclosed in Japanese Application Publication No. 2000-516486.

However, the material thickness of a stent is in general extremely small, about 100 μm. In addition, a stent in practical use receives forces in various directions from a blood vessel wall or the like. In the stents like the one disclosed in Japanese Application Publication No. 2000-516486, therefore, it may be difficult to successfully achieve the intended engagement, and the stent may be expanded nonuniformly. Thus, there has been the problem that non-uniform expansion of the stent cannot be avoided assuredly.

SUMMARY

Disclosed here is a stent positionable on an outer circumference of an inflatable balloon and expandable by inflation of the balloon, wherein the stent includes: a circumferentially extending wavy-shaped member which is expandable and contractable in the radial direction of the stent; with the circumferentially extending wavy-shaped member including a pair of straight parts, an apex part, and an opening; with the apex part possessing opposite ends each connected to one of the straight parts; with the opening located at least in the apex part; and with the apex part including a link part located to an outer circumferential side of the opening and a base part located to an inner circumferential side of the opening. The base part possesses a curved inner circumference, the link part lies across a vertex of the base part, and the link part possesses a width in relation to the circumferential direction of the stent is smaller than a width of the base part in relation to the circumferential direction of the stent, at the vertex of the base part.

According to another aspect, a stent is positionable on an inflatable balloon in surrounding relation to an outer circumference of the balloon, with the balloon being expandable by inflating the balloon. The stent includes: a plurality of annular members arranged in an axially extending manner, with axially adjacent annular members connected to one another; with each of the annular members comprised of a circumferentially extending wavy-shaped member which is expandable and contractable in the radial direction of the stent, and each of the annular members possessing one axial end and an other axial end; and wherein each of the circumferentially extending wavy members includes a plurality of curved apex parts at the one axial end of the annular member and a plurality of curved apex parts at the other axial end of the annular member. Each of the curved apex parts at the one axial end of each annular member possessing opposite ends, and each of the curved apex parts at the other axial end of each annular member possess opposite ends; and each end of each of the curved apex parts at the one axial end of each annular member are connected to one of the ends of one of the curved apex parts at the other axial end of the annular member by a member possessing at least a straight part. An opening is located in a plurality of the curved apex parts at the one axial end of each annular member, and an opening is located in a plurality of the curved apex parts at the other axial end of each annular member, with each of the openings at the one axial end being completely surrounded by material forming the curved apex of each annular member and each of the openings at the other axial end being completely surrounded by material forming the curved apex of each annular member. Each of the plurality of curved apex parts at the one axial end of each annular member, and each of the apex parts at the other axial end of each annular member include a link part located radially outwardly of the opening and a base part located radially inwardly of the opening, wherein the base part possesses a curved inner circumference, the link part lies across a vertex of the base part, and the link part and the base part both possess a width, with the width of the link part in relation to the circumferential direction of the stent being smaller than the width of the base part in relation to the circumferential direction of the stent, at the vertex of the base part.

Another aspect of the disclosure here involves a stent delivery system that includes a balloon catheter including a hollow shaft section and an inflatable balloon disposed on an outer circumference of a distal end portion of the shaft section, and a stent disposed on an outer circumference of the balloon and expanded by inflation of the balloon. The stent includes: a circumferentially extending wavy-shaped member which is expandable and contractable in the radial direction of the stent; with the circumferentially extending wavy-shaped member including a pair of straight parts, an apex part, and an opening; with the apex part possessing opposite ends each connected to one of the straight parts; with the opening located at least in the apex part; and with the apex part including a link part located to an outer circumferential side of the opening and a base part located to an inner circumferential side of the opening. The base part possesses a curved inner circumference, the link part lies across a vertex of the base part, and the link part possesses a width in relation to the circumferential direction of the stent is smaller than a width of the base part in relation to the circumferential direction of the stent, at the vertex of the base part.

According to the stent disclosed here, when deformation is concentrated in certain of the apex parts and nonuniform expansion is about to be generated at the time of expansion of the stent, the link part disposed at the apex part in which the deformation is concentrated displays a springy action (elasticity), whereby plastic deformation of the base part of the apex part in which the deformation is concentrated is restrained. This helps promote deformation of the other apex parts (the apex parts where plastic deformation amount and link part's springy action are relatively smaller), resulting in that uniform expansion is achieved. Specifically, in the stent disclosed here, the base part has a curved inner circumference, the link part lies across the vertex of the base part, and the width of the link part in relation to the circumferential direction of the stent is smaller than the width of the base part in relation to the circumferential direction of the stent, at the vertex of the base part. This helps ensure that the springy action of the link part can be displayed effectively. In addition, since mechanical operational element (for example, engagement) is not utilized for uniform expansion, even if the material thickness of the stent is small or the stent receives forces in various directions from a blood vessel wall or the like in practical use of the stent, the influences of the small material thickness or the forces are limited. In short, it is possible to provide a stent and a stent delivery system by which uniform expansion can be achieved reliably.

Preferably, the outer circumference of that portion of the link part which is opposite to the vertex has a curved shape. In this case, the springy action of the link part can be displayed effectively.

The radius of curvature of the outer circumference of the link part is preferably greater than the radius of curvature of the inner circumference of the base part. The springy action of the link part will thus be favorable, and plastic deformation of the base part will proceed smoothly.

The linear member preferably constitutes an annular body, and a plurality of such annular bodies are arranged along the axial direction of the stent. In this case, the strength with which the stent is fixed to the balloon (stent retaining force) can be enhanced, and drop-off of the stent from the balloon can be restrained reliably.

The annular bodies adjacent to each other along the axial direction of the stent are preferably integrated through a connecting part. The strength with which the stent is fixed to the balloon (stent retaining force) can thus be enhanced, and drop-off of the stent from the balloon can be restrained assuredly.

Preferably, some of the apex parts are connected to one of the connecting part and some of the apex parts are not connected to any of the connecting parts. The apex parts will this be relatively easily deformed, so that the stent will be expanded more easily.

Further features, aspects and advantages of the stent and stent delivery system disclosed here will become apparent by referring to the preferred embodiment described below and illustrated in the accompanying drawings.

DETAILED DESCRIPTION

Figure 1:
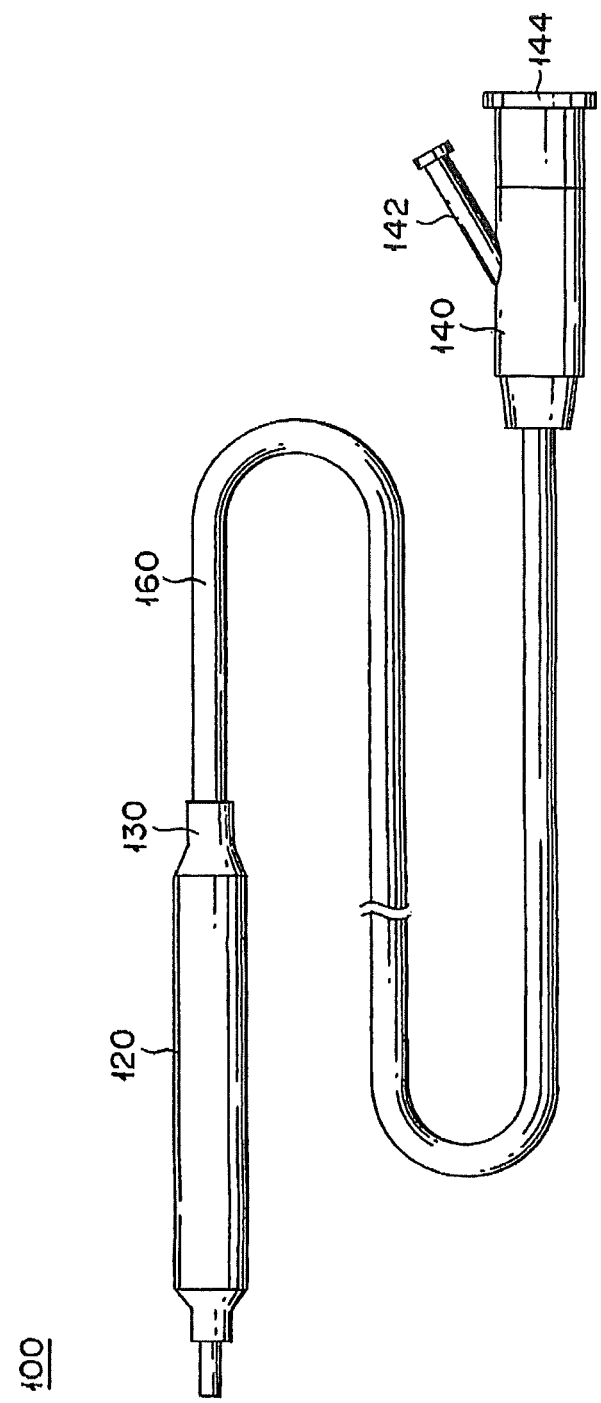
FIG. 1 is a plan view of a stent delivery system according to an embodiment disclosed here.
Figure 2:
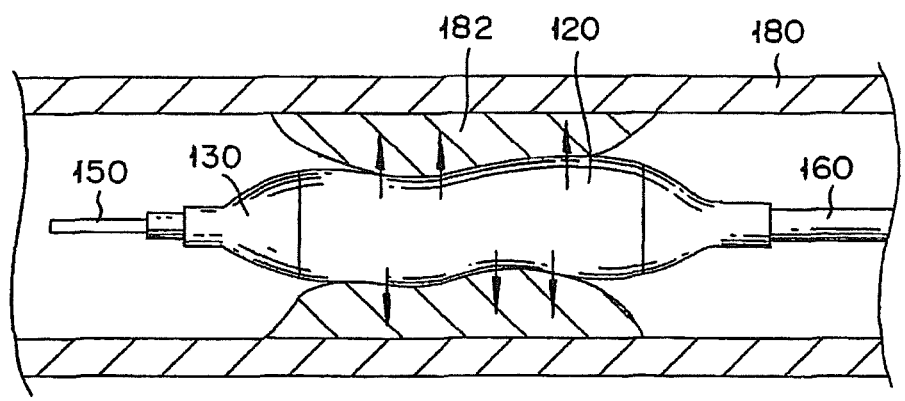
FIG. 2 is a partial cross-sectional view illustrating a use for the stent delivery system shown in FIG. 1.

Referring initially to FIGS. 1 and 2, the stent delivery system 100 according to one embodiment disclosed here by way of example is used to improve a stenosis (or occluded part) 182 generated in a lumen 180 in a living body (see FIG. 2). As shown in FIG. 1, the stent delivery system 100 includes a tubular shaft (shaft section) 160, a balloon 130 disposed on the outer circumference of a distal end portion of the tubular shaft 160, a stent 120 disposed on the outer circumference of the balloon 130, and a hub 140 located at a proximal portion of the tubular shaft 160.

The lumen 180 in the living body is, for example, a coronary artery of the heart. One of the purposes of indwelling the stent 120 in the lumen of the living body is to prevent restenosis after PTCA (Percutaneous Transluminal coronary Angioplasty). The mode of using the stent delivery system 100 is not restricted to the mode of applying it to a stenosis generated in the coronary artery of the heart, and it may be applied also to a stenosis generated in other blood vessels, bile duct, trachea, esophagus, urethra and the like.

The stent 120 is a medical device to be put indwelling in secure contact with the inner surface of the stenosis 182, to thereby maintain the patency (open condition) of the lumen 180. The stent 120 is configured to be expandable. The stent 120 is engaged with the balloon 130 so as to restrain positional deviation or peeling (separation) of the stent 120 from the balloon 130. The stent 120 is so configured that uniform expansion thereof can be securely achieved, as described later.

The balloon 130 is so configured that it can be freely inflatable so as to expand, and to enlarge the radius of, the stent 120 disposed on the outer circumference thereof.

The hub 140 has an injection port 142 and a guide wire port 144. The injection port 142 is used, for example, for introducing and discharging a pressure fluid which is used for inflating the balloon 130. The pressure fluid is, for example, a liquid such as physiological saline and an angiographic contrast agent. The guide wire port 144 is used for inserting a guide wire 150 into the tubular shaft 160 and protruding the guide wire 150 beyond a distal end portion of the tubular shaft 160.

Putting the stent 120 in the lumen of the living body (i.e., indwelling the stent) is carried out, for example, as follows.

First, a distal end portion of the stent delivery system 100 is inserted into the lumen 180 of a patient, and is positioned into the stenosis 182, which is the target part, while the guide wire 150 having preliminarily been protruded beyond the distal end portion of the tubular shaft 160 is advanced in a preceding manner. Then, the pressure fluid is introduced via the injection port 142 to inflate the balloon 130, thereby causing expansion and plastic deformation of the stent 120, whereby the stent 120 securely contacts the stenosis 182 (see FIG. 2). Thereafter, the balloon 130 is deflated, to disengage the stent 120 and the balloon 130 from each other, thereby separating the stent 120 from the balloon 130. As a result, the stent 120 is set indwelling (indwelled) in the stenosis 182. Then, the stent delivery system 100 from which the stent 120 has thus been separated is moved backward, to be removed from the lumen 180.

Figure 3:
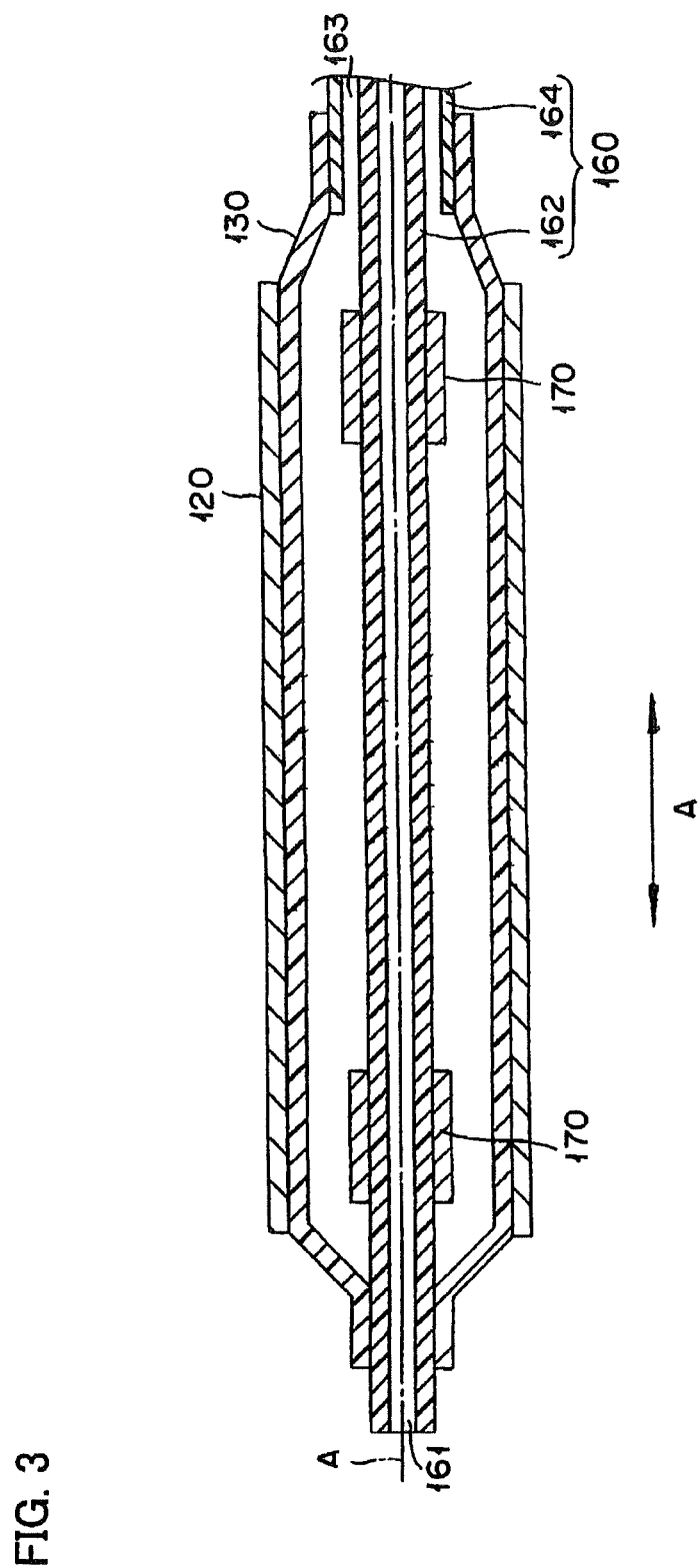
FIG. 3 is a longitudinal cross-sectional view of the distal end portion of the stent delivery system shown in FIG. 1, illustrating also the stent.

The distal end portion of the stent delivery system 100 will now be described in detail below. Referring to FIG. 3, the balloon 130 is disposed along the axial direction A in relation to the outer circumference of the distal end portion of the tubular shaft 160, in a folded state (or a contracted state), and is freely inflatable. The stent 120 is disposed on the outer circumference of the balloon 130, in a radially contracted state. With the balloon 130 inflated, a linear member in the form of a wavy-shaped member 122 of the stent 120 is expanded.

The material forming the balloon 130 is preferably a flexible material. Examples of the flexible material include polyolefin, polyvinyl chloride, polyamides, polyamide elastomers, polyurethane, polyesters such as polyethylene terephthalate, etc., polyarylene sulfides such as polyphenylene sulfide, silicone rubbers, and latex rubber. Examples of the polyolefin include polyethylene, polypropylene, ethylene-propylene copolymer, ethylene-vinyl acetate copolymer, and crosslinked ethylene-vinyl acetate copolymer.

The stent 120 is formed from a biocompatible material. Examples of the biocompatible material include nickel-titanium alloys, cobalt-chromium alloys, stainless steels, iron, titanium, aluminum, tin, and zinc-tungsten alloys.

The tubular shaft 160 includes an inner tube 162, and an outer tube 164 in which the inner tube 162 is positioned. The inner tube 162 communicates with the guide wire port 144 of the hub 140, and penetrates the balloon 130 to extend to the distal end of the balloon 130. Therefore, the guide wire 150 inserted in the guide wire port 144 can freely protrude beyond the distal end of the stent delivery system 100, and the inside of the inner tube 162 constitutes a guide wire lumen 161.

Cylindrical markers 170 are mounted on the outer circumference of the inner tube 162, inside the balloon 130. The markers 170 are formed from a radiopaque material, so that clear contrast images of them can be obtained under radioscopy. This helps ensure that the positions of the balloon 130 and the stent 120 can be rather easily confirmed. Examples of the radiopaque material include platinum, gold, tungsten, iridium, and their alloys.

The outer tube 164 is disposed outside the inner tube 162. A space exists between the inner circumferential surface of the outer tube 164 and the outer circumferential surface of the inner tube 162, and this space defines a lumen 163 which communicates with the injection port 142 of the hub 140. The balloon 130 is fixed in a liquid-tight manner to the outer circumference of the distal end portion of the inner tube 162 and to the outer circumference of the distal end portion of the outer tube 164. The inside of the balloon 130 communicates with the lumen 163. Therefore, the pressure fluid introduced via the injection port 142 can pass through the lumen 163, to be introduced into the inside of the balloon 130, thereby inflating the balloon 130. The method of fixing the balloon 130 to the outer circumferences of the distal end portions of the inner tube 162 and the outer tube 164 is not specifically restricted; for example, an adhesive or heat fusing may be employed.

The material constituting the outer tube 164 is preferably a flexible material. Examples of the flexible material include polyolefins such as polyethylene, polypropylene, polybutene, ethylene-propylene copolymer, ethylene-vinyl acetate copolymer, ionomers, mixtures of two or more of them, etc., thermoplastic resins such as soft polyvinyl chloride resin, polyamides, polyamide elastomers, polyesters, polyester elastomers, polyurethane, fluororesins, etc., silicone rubbers, and latex rubber.

As the material constituting the inner tube 162, the same materials as those for the outer tube 164 and metallic materials are applicable. Examples of the metallic materials include stainless steels and Ni—Ti alloys.

Examples of the material constituting the hub 140 (see FIG. 1) include thermoplastic resins such as polycarbonate, polyamides, polysulfones, polyarylates, and methacrylate-butylene-styrene copolymer.

Figure 4:
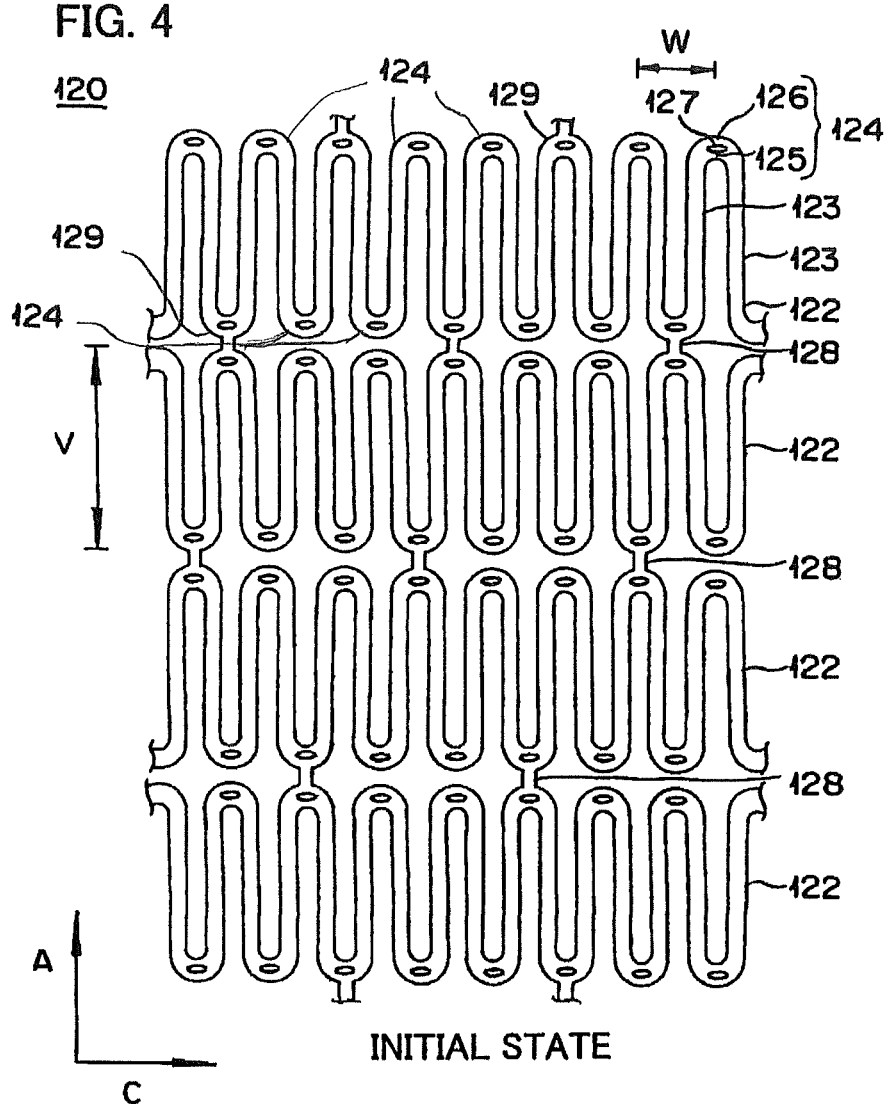
FIG. 4 is a partial development view illustrating an initial state of the stent shown in FIG. 3.

Now, the stent 120 will be described in detail below. Referring to FIG. 4, the stent 120 includes linear members 122 that are wavy-shaped and extend in the circumferential direction C of the stent and which can be expanded and contracted in the radial direction of the stent. The wavy-shaped members 122 constitute an annular body. A plurality of such annular bodies are arranged along the axial direction A, and the axially adjacent annular bodies are integrated or connected to each other through connecting parts 128. This helps ensure that the strength with which the stent is fixed to the balloon 130 (stent retaining force) is enhanced, and drop-off of the stent from the balloon 130 is securely restrained.

Each wavy-shaped member 122 includes a plurality of circumferentially spaced apart straight parts 123, a plurality of circumferentially spaced apart apex parts 124 and 129 at both axial ends of the wavy-shaped member 122, and an opening 127 at the apex parts 124, 129. As shown in FIG. 4, each end of each apex part 124, 129 is connected to one of the straight parts 123. In the illustrated embodiment representing an example of the stent, an opening 127 is preferably located in each of the apex parts 124, 129. The apex parts 124, 129 each include a link part 126 composed of a portion of the apex part which is located on the outer circumferential side relative to the opening 127, and a base part 125 composed of a portion of the apex part which is located to the inner circumferential side relative to the opening 127. The opening 127 is preferably provided in every one of the apex parts 124 and 129 of the wavy-shaped members 122.

As shown in FIG. 4, each opening 127 is elliptical in shape. In addition, in this disclosed and illustrated embodiment, the straight parts 123 are straight over their entire length. But it is also sufficient that the straight parts 123 are straight in shape at least along a part of their length, particularly in the vicinity of both ends of the straight part connected to the apex parts 124 and 129. Thus, the straight parts 123 may have a gently curved portion at their intermediate portion, for example.

Figure 5:
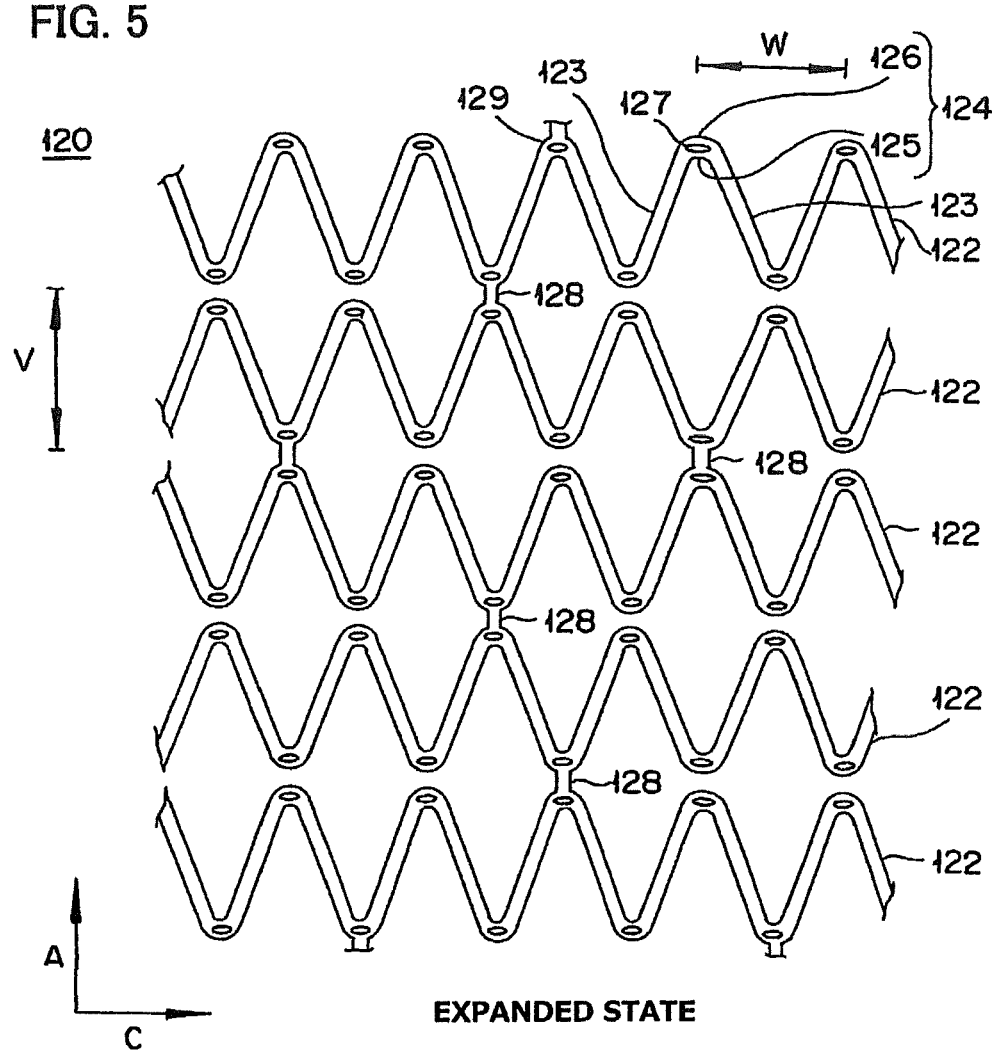
FIG. 5 is a partial development view illustrating an expanded state of the stent shown in FIG. 3.

The wavelength W, or the distance between the apexes (apex points) of apex parts 124 and 129 that are circumferentially adjacent each other in the circumferential direction C of the stent, is substantially constant. Similarly, the amplitude V, or the distance between the apexes (apex points) of the apex parts 124 and 129 located at (connected to) opposite ends of the straight part 123, is substantially constant. When the stent is expanded, the wavy-shaped member 122 deforms as shown in FIG. 5. Specifically, as the radial expansion of the stent 120 progresses, end portions of the straight parts 123 are spaced away from each other (diverge from one another), with each of the apex parts 124 and 129 as a center. This results in the amplitude V being shortened as the wavelength W is elongated or increased.

Figure 6:
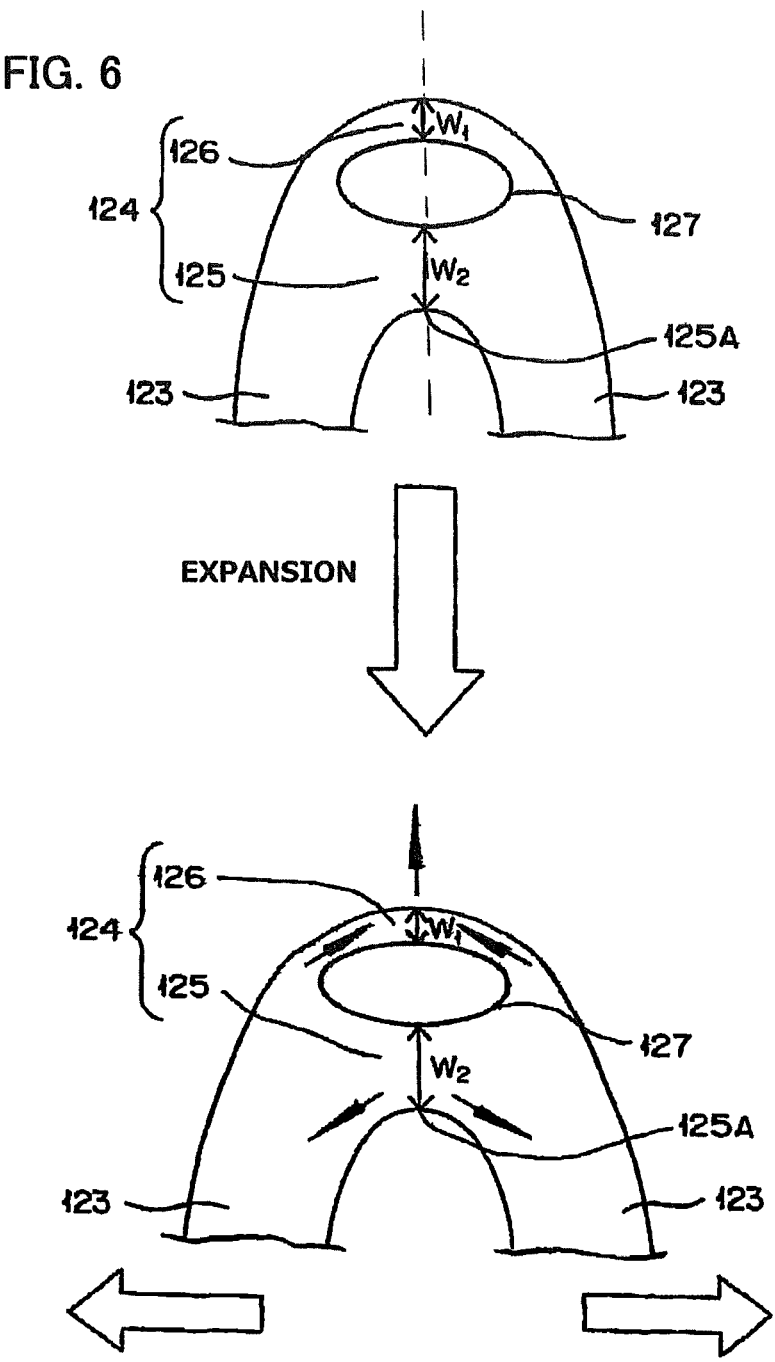
FIG. 6 is a somewhat conceptual view illustrating the deformation of a wavy-shaped linear member shown in FIG. 5 into an expanded state.

In this instance, when deformation is concentrated in certain of the apex parts 124 and 129 and nonuniform expansion is about to be generated, as shown in FIG. 6, the link part 126 disposed at each of the apex parts 124 and 129 in which the deformation is concentrated displays a springy action (elasticity), whereby plastic deformation of the base part 125 of each of the apex parts 124 and 129 in which the deformation is concentrated is restrained. This promotes deformation of the other apex parts (the apex parts where plastic deformation amount and link part's springy action are relatively smaller), resulting in uniform expansion being achieved. In addition, since mechanical operational element (for example, engagement) is not utilized for uniform expansion, even if the material thickness of the stent 120 is relatively small or the stent receives forces in various directions from a blood vessel wall or the like in practical use of the stent, the influences of the small material thickness or the forces are limited.

Therefore, uniform expansion is securely achieved. As a result, when the stent 120 is disposed in the lumen 180 so as to expand the lumen 180, for example, the force for expanding the inner surface of the lumen 180 (stenosis 182) (for example, a blood vessel expanding force) can be applied properly (see FIG. 2).

Figure 7:
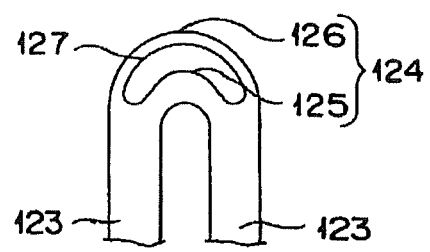
FIG. 7 is an illustration of modification 1 according to another embodiment disclosed here.

Preferably, the inner circumference of the base part 125 is curved, the outer circumference of the link part 126 at a portion opposite to the vertex 125A is curved, and the link part 126 is so disposed as to lie across or cross a line (the dotted line shown in FIG. 6) connecting the vertex 125A of the inner circumference of the base part 125 (which is an inflection point of the base part 125) with the vertex of the outer circumference of the link part 126 (which is an inflection point of the link part 126). In this case, the springy action of the link part 126 can be displayed effectively. As shown in FIGS. 6 and 7, the link parts 126, as well as the base parts 125, are uninterrupted between opposite ends connected to the straight parts 122.

The radius of curvature of the outer circumference of the link part 126 is preferably greater than the radius of curvature of the inner circumference of the base part 125. In this case, the springy action of the link part 126 will be favorable, and plastic deformation of the base part 125 will proceed rather smoothly. The width W1 (radial dimension) of the link part 126 in relation to the radial direction of the stent at the vertex of the link part 126 is preferably smaller than the width W2 (radial dimension) of the base part 125 in relation to the radial direction of the stent, at the vertex 125A of the base part 125 as shown in FIG. 6. In this case, the springy action of the link part 126 will be more favorable.

As shown in FIGS. 4 and 5, the wavy-shaped member 122 includes the apex parts 129 which are connected to the connecting part 128 and the apex parts 124 which are not connected to the connecting part 128. Therefore, the apex parts 124 and 129 will be deformed relatively easily so that the stent will be expanded more easily.

The method for forming the wavy-shaped member 122 is not specifically restricted. The wavy-shaped member 122 can be formed, for example, by a method in which the outer circumference of a tubular stent material is subjected to laser beam cutting on the basis of the pattern of the wavy-shaped members 122, or by a method in which a masking material corresponding to the pattern of the wavy-shaped members 122 is disposed on the outer circumference of a tubular stent material and etching is conducted.

Figure 8:
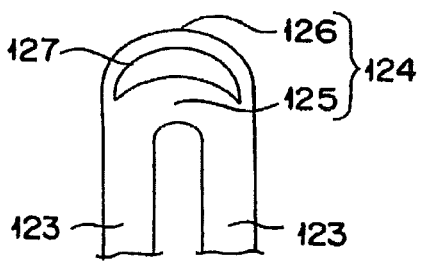
FIG. 8 is an illustration of modification 2 according to an additional embodiment disclosed here.
Figure 9:
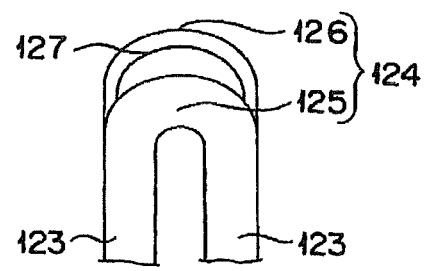
FIG. 9 is an illustration of modification 3 according to a further embodiment disclosed here.

Now, several modifications to the disclosed stent will be described below. The modifications are illustrated in FIGS. 7-9. The shape of the opening 127 is not restricted to an ellipse. For instance, the shape may be a shape obtained by curving a central portion of an ellipse such as shown in FIG. 7 or a crescent as shown in FIG. 8. In addition, the link part 126 is not restricted to the one that is formed integral with the base part 125 (wavy-shaped member 122); thus, a link part 126 formed as a separate body may be joined to the base part 125 (the apex part 124). The opening 127 may be so configured as to extend beyond the apex part 124 to the straight part 123, if necessary. In this case, the end portions of the link part 126 are connected to the straight parts 123.

As described above, the stent and stent delivery system disclosed here makes it possible to reliable achieve relatively uniform expansion.

The present invention is not restricted to the above-described embodiment, and various alterations are possible within the scope of the claims. For instance, the balloon catheter is applicable not only to the over-the-wire (OTW) type but also to the rapid exchange (RX) type.

The stent may be formed from a biodegradable polymer which is dissolved and absorbed in a living body with the lapse of time, or the stent surface may be coated with a drug (biologically active agent). Examples of the biodegradable polymer include polylactic acid, polyglycolic acid, and lactic acid-glycolic acid copolymer. Examples of the drug include carcinostatic agents, immunosuppressors, antibiotics, immunosuppressors, and antithrombogenic agents. Furthermore, a marker may be disposed on the proximal side of the tubular shaft.

The detailed description above describes a stent and stent delivery system disclosed by way of example. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A stent positionable on an outer circumference of an inflatable balloon and expandable by inflation of the balloon, the stent comprising:

a plurality of annular bodies, each of said plurality of annular bodies including a circumferentially extending wavy-shaped member which is expandable and contractable in the radial direction of the stent, said plurality of annular bodies being arranged along an axial direction of the stent;

each of the circumferentially extending wavy-shaped members including a pair of straight parts and an apex part;

each said apex part possessing opposite ends each connected to one of the straight parts and only a single opening having an elliptical shape being located at least in the apex part;

each said apex part including a link part located to an outer circumferential side of the single opening and a base part located to an inner circumferential side of the single opening, the base part being uninterrupted and possessing a curved inner circumference, the link part lying across a vertex of the base part, and the link part possessing a width extending from the outer circumferential side of the single opening to a vertex of the apex part that is smaller than a width of the base part extending from the inner circumferential side of the single opening to the vertex of the base part; and a plurality of connecting parts, each of which is disposed between axially adjacent annular bodies;

wherein said connecting parts interconnect axially aligned link parts of said axially adjacent annular bodies;

wherein the elliptical shape of the single opening has a major axis extending along the circumferential direction of the stent and a minor axis extending along the longitudinal direction of the stent.

2. The stent according to claim 1, wherein a portion of each said link part positioned at the vertex of the apex part has a curved outer circumference.

3. The stent according to claim 2, wherein the curved outer circumference of each said link part possesses a radius of curvature greater than a radius of curvature of the curved inner circumference of each said base part.

4. The stent according to claim 1, wherein each said wavy-shaped member includes apex parts connected to one of the connecting parts and apex parts not connected to any of the connecting parts.

5. The stent according to claim 1, wherein at least some of said openings extend towards said straight parts.

6. A stent positionable on an inflatable balloon in surrounding relation to an outer circumference of the balloon, the balloon being expandable by inflating the balloon, the stent comprising:

a plurality of annular members arranged in an axially extending manner, with axially adjacent annular members connected to one another;

each of the annular members being comprised of a circumferentially extending wavy-shaped member which is expandable and contractable in the radial direction of the stent, each of the annular members possessing one axial end and an other axial end;

each of the circumferentially extending wavy members including a plurality of curved apex parts at the one axial end of the annular member and a plurality of curved apex parts at the other axial end of the annular member;

each of the curved apex parts at the one axial end of each annular member possessing opposite ends, and each of the curved apex parts at the other axial end of each annular member possessing opposite ends;

each end of each of the curved apex parts at the one axial end of each annular member being connected to one of the ends of one of the curved apex parts at the other axial end of the annular member by a member possessing at least a straight part;

only a single opening located in each of a plurality of the curved apex parts at the one axial end of each annular member, and only a single opening located in each of a plurality of the curved apex parts at the other axial end of each annular member, each of the openings at the one axial end being completely surrounded by material forming the curved apex of each annular member, and each of the openings at the other axial end being completely surrounded by material forming the curved apex of each annular member, and each of the openings having an elliptical shape;

each of the plurality of curved apex parts at the one axial end of each annular member, and each of the apex parts at the other axial end of each annular member including a link part located radially outwardly of each of the single openings and a base part located radially inwardly of each of the single openings;

each said base part being uninterrupted and possessing a curved inner circumference;

each said link part lying across a vertex of the base part;

each said link part and each said base part both possessing a width, the width of each said link part extending from an outer circumferential side of the single opening to a vertex of the apex part being smaller than the width of each said base part extending from an inner circumferential side of the single opening to the vertex of the base part; and a plurality of connecting parts connecting the axially adjacent annular members;

wherein each said connecting part interconnects axially aligned said link parts of said axially adjacent annular members;

wherein the elliptical shape of each of the openings has a major axis extending along the circumferential direction of the stent and a minor axis extending along the longitudinal direction of the stent.

7. The stent according to claim 6, wherein a portion of each said link part positioned at the vertex of the apex part has a curved outer circumference.

8. The stent according to claim 7, wherein the curved outer circumference of the link part possesses a radius of curvature greater than a radius of curvature of the curved inner circumference of the base part.

9. The stent according to claim 6, wherein some of the curved apex parts at the one axial end of each annular member and some of the curved apex parts at the other axial end of each annular member are connected to the connecting parts, and some of the curved apex parts at the one axial end of each annular member and some of the curved apex parts at the other axial end of each annular member are not connected to the connecting parts.

10. The stent according to claim 6, wherein the members connecting each end of each of the curved apex parts at the one axial end of each annular member to one of the ends of one of the curved apex parts at the other axial end of the annular member is straight along its entire extent.

11. The stent according to claim 6, wherein the opening is located in all of the curved apex parts at the one axial end of each annular member and is located in all of the curved apex parts at the other axial end of each annular member.

12. The stent according to claim 6, wherein at least some of said openings extend towards said straight parts.

13. A stent delivery system comprising:

a balloon catheter including a hollow shaft section and an inflatable balloon disposed on an outer circumference of a distal end portion of the shaft section;

a stent disposed on an outer circumference of the balloon and expanded by inflation of the balloon; wherein the stent comprises:

a plurality of annular bodies, each of said plurality of annular bodies including a circumferentially extending wavy-shaped member which is expandable and contractable in the radial direction of the stent, said annular bodies being arranged along an axial direction of the stent;

each of the circumferentially extending wavy-shaped members including a pair of straight parts and an apex part;

each said apex part possessing opposite ends each connected to one of the straight parts;

only a single opening being located at least in each said apex part, each said opening having an elliptical shape, the elliptical shape of each said opening having a major axis extending along the circumferential direction of the stent and a minor axis extending along the longitudinal direction of the stent;

each said apex part including a link part located to an outer circumferential side of the opening and a base part located to an inner circumferential side of the opening;

each said base part being uninterrupted and possessing a curved inner circumference;

each said link part lying across a vertex of the base part;

the width of each said link part extending from the outer circumferential side of the single opening to a vertex of the apex part being smaller than a width of each said base part extending from the inner circumferential side of the single opening to the vertex of the base part; and a plurality of connecting parts, each of which is disposed between axially adjacent annular bodies;

wherein said connecting parts interconnect axially aligned said link parts of said axially adjacent annular bodies.

14. The stent delivery system according to claim 13, wherein at least some of said openings extend towards said straight parts.

* * * * *